US011680198B2

(12) United States Patent
Musso et al.

(10) Patent No.: US 11,680,198 B2
(45) Date of Patent: Jun. 20, 2023

(54) WATER SWELLABLE CEMENT SHEATH ON DEMAND, WITH SENSING CAPABILITY

(71) Applicant: Saudi Arabian Oil Company, Dhahran (SA)

(72) Inventors: Simone Musso, Houston, TX (US); Ashok Santra, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 950 days.

(21) Appl. No.: 16/570,783

(22) Filed: Sep. 13, 2019

(65) Prior Publication Data

US 2021/0079287 A1    Mar. 18, 2021

(51) Int. Cl.
| | | |
|---|---|---|
| E21B 33/14 | (2006.01) |
| C09K 8/467 | (2006.01) |
| E21B 47/005 | (2012.01) |
| C04B 14/02 | (2006.01) |
| C04B 14/38 | (2006.01) |
| C04B 14/48 | (2006.01) |
| C04B 22/04 | (2006.01) |
| C04B 22/06 | (2006.01) |
| C04B 28/02 | (2006.01) |
| E21B 36/04 | (2006.01) |
| C04B 111/94 | (2006.01) |

(52) U.S. Cl.
CPC ............ *C09K 8/467* (2013.01); *C04B 14/026* (2013.01); *C04B 14/386* (2013.01); *C04B 14/48* (2013.01); *C04B 22/04* (2013.01); *C04B 22/06* (2013.01); *C04B 22/064* (2013.01); *C04B 28/02* (2013.01); *E21B 33/14* (2013.01); *E21B 36/04* (2013.01); *E21B 47/005* (2020.05); *C04B 2111/94* (2013.01)

(58) Field of Classification Search
CPC ..... C09K 8/467; C04B 14/026; C04B 14/386; C04B 14/48; C04B 22/04; C04B 22/06; C04B 22/064; C04B 28/02; C04B 2111/94; C04B 2111/72; C04B 2111/74; C04B 40/0085; C04B 40/0096; C04B 40/0633; C04B 40/0641; C04B 40/0675; E21B 33/14; E21B 36/04; E21B 47/005; G01N 27/20; G01N 33/383
See application file for complete search history.

(56) References Cited

U.S. PATENT DOCUMENTS

| | | | |
|---|---|---|---|
| 8,822,386 B2 | 9/2014 | Quintero et al. | |
| 10,167,714 B2 | 1/2019 | Musso et al. | |
| 2012/0206144 A1 | 8/2012 | Barlet-Gouedard | |
| 2015/0361760 A1 | 12/2015 | Mcclung, III | |
| 2016/0340245 A1 | 11/2016 | Loh et al. | |
| 2017/0108456 A1 | 4/2017 | Alizadeh et al. | |
| 2017/0121587 A1 | 5/2017 | Allouche et al. | |
| 2017/0349805 A1 * | 12/2017 | Musso | .............. C04B 28/02 |

FOREIGN PATENT DOCUMENTS

| | | | |
|---|---|---|---|
| EP | 1933004 A1 | 6/2008 | |
| FR | 2260851 | 9/1975 | |
| WO | 2009068363 A1 | 6/2009 | |
| WO | WO-2009068363 A1 * | 6/2009 | ............ C04B 28/02 |
| WO | 2015077524 A1 | 5/2015 | |
| WO | 2015195596 A1 | 5/2015 | |
| WO | 2017137789 A1 | 8/2017 | |
| WO | WO-2017137789 A1 * | 8/2017 | ......... C04B 20/1029 |
| WO | 2018200341 A1 | 11/2018 | |
| WO | 2019076585 A1 | 4/2019 | |
| WO | WO-2019076585 A1 * | 4/2019 | ............ B01J 13/046 |

OTHER PUBLICATIONS

Guillermo Bastos et al., Admixtures in Cement-matrix Composites for Mechanical Reinforcement, Sustainability, and Smart Features, 9 Materials 972 (2016).
PCT ISR/WO Report mailed Dec. 15, 2020, in the prosecution of patent application No. PCT/US2020/050598, 18 pages.

* cited by examiner

*Primary Examiner* — Kumar R Bhushan
(74) *Attorney, Agent, or Firm* — Bracewell LLP; Constance G. Rhebergen; Eleanor L. Tyson

(57) ABSTRACT

A method of sealing propagating cracks in a sensor-laden cement sheath comprising the steps of monitoring an electrical resistivity of the sensor-laden cement sheath to produce a measured value, wherein the sensor-laden cement sheath comprises a conductive sensor, an on-demand expanding agent, and a cement, activating a heat source when the measured value of the electrical resistivity is greater than an activation threshold, increasing a temperature of the sensor-laden cement sheath with the heat source to an activation temperature, wherein the activation temperature is operable to initiate a reaction between the on-demand expanding agent and water, wherein the activation temperature is greater than a formation temperature, reacting the on-demand expanding agent with water to produce a swelled agent, wherein the swelled agent occupies a greater volume than the on-demand expanding agent, and sealing the propagating cracks in the sensor-laden cement sheath with the swelled agent.

8 Claims, 2 Drawing Sheets

WATER SWELLABLE CEMENT SHEATH ON DEMAND, WITH SENSING CAPABILITY

TECHNICAL FIELD

Disclosed are compositions and methods for use with cement. Specifically, disclosed are compositions and methods for monitoring cement in a downhole environment.

BACKGROUND

The cement sheath in a wellbore annulus, for example, between the casing and the formation wall in a wellbore, impacts the ability to control the flow of formation fluids from the reservoir. Disruptions in the cement sheath, such as radial cracks or microannulus formation, can act as a pathway for formation fluid to escape the reservoir in an uncontrolled manner.

Radial cracks can occur due to downhole stresses from overburden pressure, completion or fracturing related pressure, or from thermal changes causing uneven expansion of the casing or cement sheath. Microannulus formation can occur due to shrinkage of the cement sheath or improper displacement of mud.

Identifying the presence of these disruptions and correcting them is important to maintain the integrity of the cement sheath. Identification of some cement sheath disruptions can be directly identified by sonic logging. However, some disruptions, such as small cracks or debonding between the cement sheath and rock formation, may not be identifiable using current technologies. Remediation work to correct the cement sheath disruptions can be expensive. Remedial work can include squeezing microfine cement slurry or resins into the cement sheath to seal the cracks.

SUMMARY

Disclosed are compositions and methods for use with cement. Specifically, disclosed are compositions and methods for monitoring cement in a downhole environment.

In a first aspect, a method of sealing propagating cracks in a sensor-laden cement sheath is provided. The method includes the steps of monitoring an electrical resistivity of the sensor-laden cement sheath to produce a measured value. The sensor-laden cement sheath includes a conductive sensor, an on-demand expanding agent, and a cement. The method further includes the steps of activating a heat source when the measured value of the electrical resistivity is greater than an activation threshold, such that the measured value that is greater than the activation threshold is operable to indicate propagating cracks in the sensor-laden cement sheath, increasing a temperature of the sensor-laden cement sheath with the heat source to an activation temperature operable to initiate a reaction between the on-demand expanding agent and water, where the activation temperature is greater than a formation temperature, reacting the on-demand expanding agent with water to produce a swelled agent, where the swelled agent occupies a greater volume than the on-demand expanding agent, and sealing the propagating cracks in the sensor-laden cement sheath with the swelled agent.

In certain aspects, the step of monitoring an electrical resistivity of the sensor-laden cement sheath includes the steps of determining a measured value of an electrical resistivity of the sensor-laden cement sheath, and comparing the measured value of the electrical resistivity to an activation threshold, where the activation threshold is the electrical resistivity that corresponds to a minimum acceptable amount of propagating cracks in the sensor-laden cement sheath. In certain aspects, the conductive sensor is selected from the group consisting of carbon nanotubes, carbon fibers, graphene, metal fibers, and combinations of the same. In certain aspects, the on-demand expanding agent is selected from the group consisting of magnesium oxide, calcium oxide, and combinations of the same. In certain aspects, the heat source is selected from the group consisting of a hot fluid, electricity applications, resistive heating, microwave applications, and combinations of the same. In certain aspects, the composition further includes water-filled vesicles. In certain aspects, the on-demand expanding agent further includes an encapsulation compound. In certain aspects, the encapsulation compound is selected from the group consisting of polymeric compounds, ceramic compounds, and combinations of the same.

In a second aspect, a composition to produce a sensor-laden cement sheath is provided. The composition includes a conductive sensor, the conductive sensor operable to create an electrically conductive network, an on-demand expanding agent, the on-demand expanding agent operable to react with water, and a cement.

In certain aspects, the composition further includes thermite. In certain aspects, the composition further includes a metal oxide-type super absorber. In certain aspects, the composition further includes encapsulated expanding agents.

BRIEF DESCRIPTION OF THE DRAWINGS

These and other features, aspects, and advantages of the scope will become better understood with regard to the following descriptions, claims, and accompanying drawings. It is to be noted, however, that the drawings illustrate only several embodiments and are therefore not to be considered limiting of the scope as it can admit to other equally effective embodiments.

In the accompanying Figures, similar components or features, or both, may have a similar reference label.

DETAILED DESCRIPTION

While the scope of the apparatus and method will be described with several embodiments, it is understood that one of ordinary skill in the relevant art will appreciate that many examples, variations and alterations to the apparatus and methods described here are within the scope and spirit of the embodiments.

Accordingly, the embodiments described are set forth without any loss of generality, and without imposing limitations, on the embodiments. Those of skill in the art understand that the scope includes all possible combinations and uses of particular features described in the specification.

The compositions and methods are directed to sensor-laden cement compositions. The sensor-laden cement compositions provide a method for expanding a sensor-laden cement sheath to minimize or eliminate propagating cracks in the sensor-laden cement sheath.

Advantageously, the method of sealing propagating cracks in a sensor-laden cement sheath can provide a method for real-time monitoring of a propagating crack as the propagating crack expands through the sensor-laden cement sheath. Advantageously, the combination of conductive sensors and on-demand expanding agent provides the ability to trigger a transformation in the sensor-laden cement sheath.

As used throughout, "electrical resistivity" refers to the degree to which a material resists the flow of electric current. A low electrical resistivity indicates the material does not resist the flow of electric current. Conversely, a high resistivity indicates the material does not conduct the flow of electric current well.

As used throughout, "percolation threshold" is the minimum amount of conductive sensors needed to initiate connectivity between the conductive sensors to develop an electron flow path for electrical conductivity.

Figure 1C:
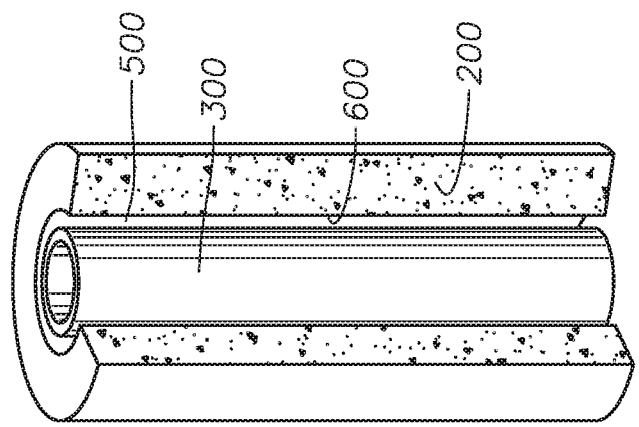
FIG. 1A-C provides a pictorial representation of different types of propagating cracks.
Figure 1B:
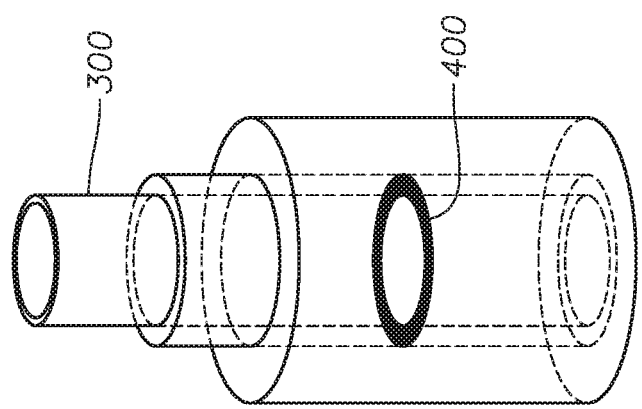
Figure 1A:
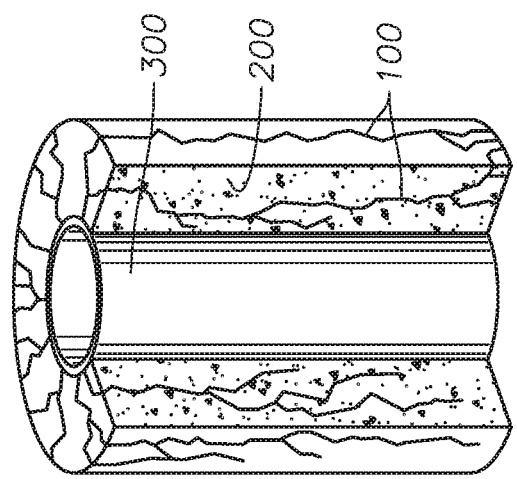

As used throughout, "propagating cracks" refers to one or more pathways in the sensor-laden cement sheath allowing fluid communication between the hydrocarbon-containing formation and the interior of the cement or the casing. Propagating cracks includes radial cracks, horizontal cracks, micro-annulus formations, and combinations of the same. The various types of propagating cracks can be understood with reference to FIGS. 1A-1C. Radial cracks 100 can occur throughout cement 200 surrounding casing 300 appearing as "veining" or "spiderwebbing." Horizontal cracks 400 can radiate outward from casing 300 as shown in FIG. 1B. Micro-annulus formations 500 can occur when cement 200 separates from casing 300 and alternately, when cement 200 separates from formation wall 600.

The sensor-laden cement composition includes a conductive sensor, an on-demand expanding agent, and a cement.

The conductive sensor can be any type of particulate that can be dispersed in cement and can be used to create an electrically conductive network through which an electrical current can flow. The conductive sensors can include carbon nanotubes, carbon fibers, graphene, metal fibers, and combinations of the same. In at least one embodiment, the conductive sensor is carbon nanotubes. Advantageously, by dispersing carbon nanotube in the sensor-laden cement sheath an electrically conductive network can be created that behaves as an electro-mechanical sensor. The conductive sensors are in the absence of encapsulation to ensure the conductive sensors are in physical contact with the cement.

The on-demand expanding agent can be any particulate material that can be dispersed in cement and react with water to produce a swelled agent. The swelled agent occupies a greater volume than the on-demand expanding agent. The particulate material can include organic materials, inorganic particulates, and combinations of the same.

Organic materials suitable for use as the on-demand expanding agent include swellable rubber, water swellable polymers, and combinations of the same. Swellable rubber can include natural rubbers and synthetic rubbers. Natural rubbers can include polyisoprene, more specifically cis-1,4-polyisoprene. Synthetic rubbers can include synthetic polyisoprene, acrylonitrile-butadiene rubber (NBR), carboxylated NBR (XNBR), hydrogenated acrylonitrile-butadiene rubber (HNBR), carboxylated HNBR (HXNBR), epichlorohydrin rubber (ECO), acrylic rubber (ACM), ethylene-propylene rubber (EPDM), chloroprene rubber, butadiene rubber, styrene-butadiene rubber, fluororubber, silicone rubber, urethane rubber, and isoprene-propylene rubber, and combinations of the same. Water swellable polymers can include polyacrylamide copolymer, ethylene maleic anhydride copolymer, cross-linked carboxymethylcellulose, polyvinyl alcohol copolymers, crosslinked polyethylene oxide, starch grafted copolymer of polyacrylonitrile, and combinations of the same.

Inorganic particulates suitable for use as the on-demand expanding agent include magnesium oxide, calcium oxide, and combinations of the same. The swelled agent of the inorganic particulates can include magnesium hydroxide ($Mg(OH)_2$), calcium hydroxide ($Ca(OH)_2$), and combinations of the same. The inorganic particulates suitable for use as the on-demand expanding agent can be present in different reactive grades. The reactive grade of the inorganic particulates can be due to the manufacturing calcination temperature. The greater the manufacturing calcination temperature the greater the degree of crystallinity and the lower the reactivity. The reactivity can influence the activation temperature of the reaction between the on-demand expanding agent and the water. In at least one embodiment, the on-demand expanding agent can be include a combination of types of inorganic particulates. In at least one embodiment, the on-demand expanding agent can include one type of inorganic material selected from across different reactive grades. In at least one embodiment, the on-demand expanding agent can include a combination of types of inorganic particulates with different reactive grades included for each type of inorganic particulates. The specific types and reactive grades of the inorganic particulates suitable for use as the on-demand expanding agent can be selected for a specific activation temperature. Advantageously, selecting a combination of types of inorganic particulates with a range of reactive grades can allow the reaction period to be tailored. Tailoring the reaction period can result in a reaction that extends for the desired length of time and alternately, in a reaction period that can be stopped and restarted as needed.

In at least one embodiment, the on-demand expanding agent can include both inorganic particulates and organic materials.

The on-demand expanding agents can be encapsulated with an encapsulation compound to produce an encapsulated expanding agent. The encapsulation compound can be any type of material suitable for encapsulating the on-demand expanding agent and delaying the interaction between water and the on-demand expanding agent. In at least one embodiment, the encapsulation compound can be permeable or semi-permeable to water, such that water permeates through the encapsulation compound and interacts with the on-demand expanding agent within the encapsulation compound. In at least one embodiment, the encapsulation compound can degrade, such that the on-demand expanding agent is exposed to water as the encapsulation compound degrades. The encapsulation compound can include polymeric compounds, ceramic compounds, polymer-ceramic composite compounds, and combinations of the same. Polymeric compounds suitable for use as the encapsulation compound include cellulosic-type polymers, degradable polymers such as polylactic acid, thermoplastic-type polymers, latex-type polymers, and combinations of the same. Ceramic compounds suitable for use as the encapsulation compound can include zirconia, silicon nitride, silicon carbide, and combinations of the same. The encapsulation compound can be selected to provide control over the reaction kinetics of the on-demand expanding agents, activation energy, and reactivity. By delaying the interaction between water and the on-demand expanding agent, the encapsulation can delay the reaction of the on-demand expanding agents with water. Advantageously, the encapsulation compound can provide additional flexibility and elasticity to the sensor-laden cement composition and the sensor-laden cement sheath. Advantageously, the encapsulation compound can act as a filler in the sensor-laden cement composition and the sensor-laden cement sheath.

In embodiments, where the encapsulation compound is a polymeric compound, the encapsulated expanding agent can be produced according to the following method. The polymeric compound can be heated to a temperature greater than its glass transition temperature to produce a softened polymeric compound. The on-demand expanding agent can be mixed with the softened polymeric compound to produce a dispersed polymeric mixture, such that in the dispersed polymeric mixture the on-demand expanding agent is dispersed throughout the softened polymeric compound. The dispersed polymeric mixture is reduced to a temperature less than the glass transition temperature of the polymeric compound to produce a cooled dispersion. The cooled dispersion can be ground to produce the encapsulated expanding agents, such that the grinding can produce encapsulated expanding agents of the desired particle size.

In at least one embodiment, the sensor-laden cement composition can include on-demand expanding agents. In at least one embodiment, the sensor-laden cement composition can include encapsulated expanding agents. In at least one embodiment, the sensor-laden cement composition can include a combination of on-demand expanding agents and encapsulated expanding agents.

The cement can be any cement suitable for use in a wellbore cementing operation. Suitable cements are those that can undergo a curing process to produce a cement sheath.

The water-filled vesicles can be any type of component capable of holding water in a cement composition. The water-filled vesicles can include an outer shell surrounding a droplets of water. The outer shell can be formed of any material capable of storing and releasing water. Examples of materials suitable for use as the outer shell can include cellulose, super absorbing polymers, and combinations of the same. Super absorbing polymers are also known as super absorbent polymers. In at least one embodiment, the water-filled vesicles can include the droplets of water when the water-filled vesicles are mixed with the sensor-laden cement composition. In at least one embodiment, the water droplets can enter the water-filled vesicles as the cement cures to produce the sensor-laden cement sheath. The water-filled vesicles can provide an internal source of water for the reaction with the on-demand expanding agents. In at least one embodiment, the sensor-laden cement sheath is in the absence of sufficient water to react with the on-demand expanding agents and water can flow from the water-filled vesicles to the cured cement sheath and act as a reactant. In at least one embodiment, where the outer shell is composed of cellulose, the cellulose can degrade at the activation temperature and release the water into the sensor-laden cement sheath. As water in the surrounding cement is depleted, the water can be drawn from water-filled vesicles into the surrounding cement.

In at least one embodiment, the sensor-laden cement composition can include thermite, such that the thermite can be dispersed and embedded in the sensor-laden cement sheath. The thermite can be encapsulated by the encapsulation compound. In at least one embodiment, metal oxide-type super absorbers can be mixed with the sensor-laden cement composition, such that the metal oxide-type super absorbers are dispersed and embedded throughout the sensor-laden cement sheath. In at least one embodiment, the metal oxide-type super absorber can be an iron oxide particle.

A method of preparing the sensor-laden cement composition is described. In one method of preparing the sensor-laden cement composition, the conductive sensors can be mixed with water to produce a sensor-containing water. Advantageously, mixing the conductive sensors with water before the cement can minimize air pollution by reducing the amount of nanoparticles that are released in the air. In at least one embodiment, the sensor-containing water can be subjected to sonication to separate the conductive sensors and increase the uniformity of the sensor-containing water. The on-demand expanding agents can be mixed with the cement to produce an agent-cement mix. The agent-cement mix can then be mixed into the sensor-containing water to produce the sensor-laden cement composition. In alternate method of preparing the sensor-laden cement composition, the conductive sensors can be mixed with water to produce a sensor-containing water and then the on-demand expanding agents can be mixed with the sensor-containing water to produce a sensor-agent water mixture. Mixing the on-demand expanding agents with the sensor-containing water can increase the amount of water absorbed by the on-demand expanding agents. Then the cement can be mixed with the sensor-agent water mixture to produce the sensor-laden cement composition. The sensor-agent water mixture can be prepared in embodiments where the on-demand expanding agents can be exposed to water before being mixed with the cement.

The conductive sensors can be present in the sensor-laden cement composition at a concentration not greater than 1 percent by weight of cement (% BWOC), alternately between 0.1% BWOC and 1% BWOC, and alternately between 0.1% BWOC and 0.99% BWOC. The concentration of conductive sensors in the sensor-laden cement composition is based on the need to cross a percolation threshold for a conductive network. Concentrations greater than 1% BWOC would not have an impact on the conductive network. The on-demand expanding agents can be present in the sensor-laden cement composition at a concentration between 8% BWOC and 25% BWOC, alternately between 10% BWOC and 25% BWOC, alternately between 10% BWOC and 15% BWOC, alternately between 15% BWOC and 20% BWOC, and alternately between 20% BWOC and 25% BWOC.

A method of producing a sensor-laden cement sheath is described. In a first step, the sensor-laden cement composition can be used in any type of cementing operation undertaken in a wellbore. The wellbore can traverse a hydrocarbon-containing formation, such that the wellbore provides fluid communication between the hydrocarbon-containing formation and the surface. The sensor-laden cement composition can be pumped into an annulus of a wellbore between a casing and the formation wall and alternately into an annulus of a wellbore between two casing strings. The step of pumping the sensor-laden cement composition into the annulus can include the equipment and steps standard for introducing a standard cement composition into an annulus of a wellbore.

The sensor-laden cement composition is then allowed to cure under the curing conditions to produce the sensor-laden cement sheath. The curing conditions can include temperature, moisture content, cure period, and combinations of the same. The curing conditions can be in the same range as a standard wellbore cement in the absence of conductive fibers or on-demand expanding agents. The curing conditions can be selected based on the conditions in the wellbore, the type of cement selected, and the desired final properties of the sensor-laden cement sheath.

A method of sealing propagating cracks in a sensor-laden cement sheath is provided. In a first step, the electrical resistivity is monitored. The electrical resistivity can be monitored in real-time and in-situ. The electrical resistivity can be monitored at any interval suitable for providing the desired data and can be based on the properties of the sensor-laden cement sheath and the wellbore conditions.

During the step of monitoring the electrical resistivity, a measured value of an electrical resistivity of the sensor-laden cement sheath can be determined. Any method useful for determining a measured value of the electrical resistivity of a material can be used. The measured value of the electrical resistivity of the sensor-laden cement sheath provides an indirect measure of the mechanical stress and strain in the sensor-laden cement sheath, which cannot be directly measured. In at least one embodiment, the electrical resistivity is measured using transmitting electrodes and receiving electrodes in electrical connection with the sensor-laden cement sheath. The transmitting electrodes and receiving electrodes can be attached to the casing before the sensor-laden cement is introduced to the wellbore. The transmitting electrodes and receiving electrodes can be any type of conductor through which electricity can enter or exit the sensor-laden cement sheath. A current can be introduced through one or more of the transmitting electrodes. Because the conductive sensors are in physical contact with the cement throughout the sensor-laden cement sheath the introduced current can travel through the conductive sensors to one or more of the receiving electrodes. The receiving electrodes can detect the current and send a signal to the surface. The measure of electrical resistivity can be determined by measuring the electrical resistance and the impedance. The signal strength can be related to the applied voltage, the intrinsic restivity of the material, and the detected damages. The measurements can be detected on the time frame of a fraction of a second. The conductive sensors enhance the introduced current and enable the in-situ measurement of the stress and strain on the sensor-laden cement sheath. Without being bound to a particular theory, the propagating cracks disrupt the network produced by the conductive sensors dispersed in the sensor-laden cement sheath resulting in a weaker current being sensed by the receiving electrodes. Advantageously, the step of determining a measured value of an electrical resistivity of the sensor-laden cement sheath can be performed in real-time and continuously. The specific interval at which current is introduced through one or more of the transmitting electrodes can be determined based on the wellbore conditions and the properties of the sensor-laden cement sheath.

In a second step of monitoring the electrical resistivity, the measured value of the electrical resistivity can be compared to an activation threshold for the sensor-laden cement sheath. The activation threshold can be a value for the electrical resistivity of the sensor-laden cement sheath based on laboratory testing of the specific sensor-laden composition allowed to cure under the cure conditions for the desired wellbore and the conditions of the wellbore. The activation threshold is the electrical resistivity that corresponds to the minimum acceptable amount of propagating cracks in the sensor-laden cement sheath. The activation threshold provides a qualitative measure of the propagating cracks. A measured value that is less than the activation threshold indicates the amount of propagating cracks is less than the minimum acceptable amount. A measure of the electrical resistivity that is greater than the activation threshold indicates the amount of propagating cracks is greater than the minimum acceptable amount. The comparison of the measured value to the activation threshold can be done by hand or can be done by computer. Advantageously, the use of conductive sensors enables the real-time, in-situ evaluation of the mechanical stress and strain in the sensor-laden cement sheath. In at least one embodiment, the comparison of the measured value to the activation threshold is performed continuously and concurrently with the step of determining a measured value of the electrical resistivity of the sensor-laden cement sheath. While the measured value is less than the activation threshold no further steps are taken and the step of monitoring the electrical resistivity can continue.

When the measured value is greater than the activation threshold, the heat source can be activated. The heat source can be any source suitable to produce heat such that the heat can increase a temperature of the sensor-laden cement sheath to an activation temperature. The heat source can be a direct heating source or an indirect heating source. Examples of sources suitable to produce heat include a hot fluid, electricity applications, resistive heating, microwave applications, and combinations of the same.

Hot fluids can be introduced to the inner casing of the wellbore, where the heat from the hot fluids can radiate through the casing to the sensor-laden cement sheath and then through the sensor-laden cement sheath. Examples of hot fluids include hot liquids and steam. The temperature of the hot fluids can be determined based on the desired activation temperature. Advantageously, hot fluids are common on a well site and the temperature can be adjusted to the desired activation temperature.

Electricity applications can include activating an electric network and initiating thermite reactions. Activating an electric network can use electricity to activate the electric network formed by the conductive sensors dispersed in the sensor-laden cement sheath. Applying electricity to produce an electric field in the sensor-laden cement sheath can generate heat due to the Joule effect. The current applied to activate the electric network is greater than the current applied to measure the electrical resistivity. Advantageously, applying electricity to increase the temperature to the activation temperature uses the same system that is used to measure the electrical resistivity. Initiating thermite reactions can use electricity to ignite thermite resulting in an exothermic reduction-oxidation reaction. The thermite can be dispersed in the fluids in the casing, alternately dispersed in the sensor-laden cement sheath, and alternately delivered by wireline to the fluids in the casing of a targeted zone. The heat produced by the exothermic reduction-oxidation reaction of thermite in the fluids in the casing can increase the temperature of fluids, such that heat flows through the casing and into the sensor-laden cement sheath. The heat produced by the exothermic reduction-reaction can increase the temperature of the sensor-laden cement sheath surrounding the thermite.

Resistive heating can use an electrical heating coil deployed via wireline tools to heat the fluid in the casing at a targeted zone. The heat can flow from the fluid through the casing and into the sensor-laden cement sheath. By controlling the size of the electrical heating coil and the location in the casing where it is deployed, the use of resistive heating can increase the temperature of sensor-laden cement sheath in only the targeted zone. Heating the sensor-laden cement sheath in targeted zones provides better control of the reactions of the on-demand expanding agents, by limiting the section of the sensor-laden cement sheath where the reactions occur.

A microwave source can be deployed in the casing via wireline tools, such that the microwave source produces microwave energy in a targeted zone. In at least one embodiment, the microwave energy can heat fluids in the casing at the targeted zone. The heat flows from the fluid through the casing and into the sensor-laden cement sheath. In an embodiment using metal oxide-type super absorbers in the sensor-laden cement sheath, the microwave energy can be absorbed by the metal oxide-type super absorber and increase the temperature of the metal oxide-type super absorbers. The heat can flow from the metal oxide-type super absorbers to the sensor-laden cement sheath and increase a temperature of the sensor-laden cement sheath. In an embodiment using metal oxide-type super absorbers and a microwave source, the casing can be fully or partially transparent to microwave energy. Using a microwave source to produce microwave energy in a targeted zone can allow for better control of the reactions the on-demand expanding agents, by limiting the section of the sensor-laden cement sheath where the reactions occur.

Applying a combination of heat sources can be used to control the reaction time, the time for heating, the location of the targeted zone, the number of targeted zones, and a combination of the same. The specific heat source selected can be based on the desired increase in temperature, the time for heating, the location of the targeted zone, the number of targeted zones, and combinations of the same.

The activation temperature is the temperature at which the reaction between the on-demand expanding agents and water is initiated. The activation temperature is determined by the composition of the on-demand expanding agent, including the types of particulate material, the different reactive grades for the types of particulate material, and the presence of encapsulated expanding agents. The activation temperature is greater than a formation temperature to ensure the reaction between the on-demand expanding agent and water is initiated by activating the heat source and not due to the ambient temperature of the sensor-laden cement sheath before the heat source is activated.

In embodiments that include the use of encapsulated expanding agents, where the encapsulation compound degrades, the activation temperature can be the temperature at which the encapsulation compound degrades. After the encapsulation compound degrades, the on-demand expanding agent can be exposed to the activation temperature. In at least one embodiment, a first activation temperature can be the temperature at which the encapsulation compound degrades and a second activation temperature can be the temperature to trigger the expanding agent, where the first activation temperature is less than the second activation temperature.

After the temperature of the sensor-laden cement sheath is increased to the activation temperature, the reaction between the on-demand expanding agent and water is initiated. The water can be the water present in the pores of the sensor-laden cement sheath or can be from the water-filled vesicles. The reaction between the on-demand expanding agent and water can produce the swelled agent. The swelled agent can occupy a greater volume than the on-demand expanding agent occupied.

The swelled agents can seal the propagating cracks by filling the space of the propagating cracks and alternately can apply a force in the sensor-laden cement sheath causing the cement in the sensor-laden cement sheath to move to fill the space of the propagating cracks.

Figure 2:
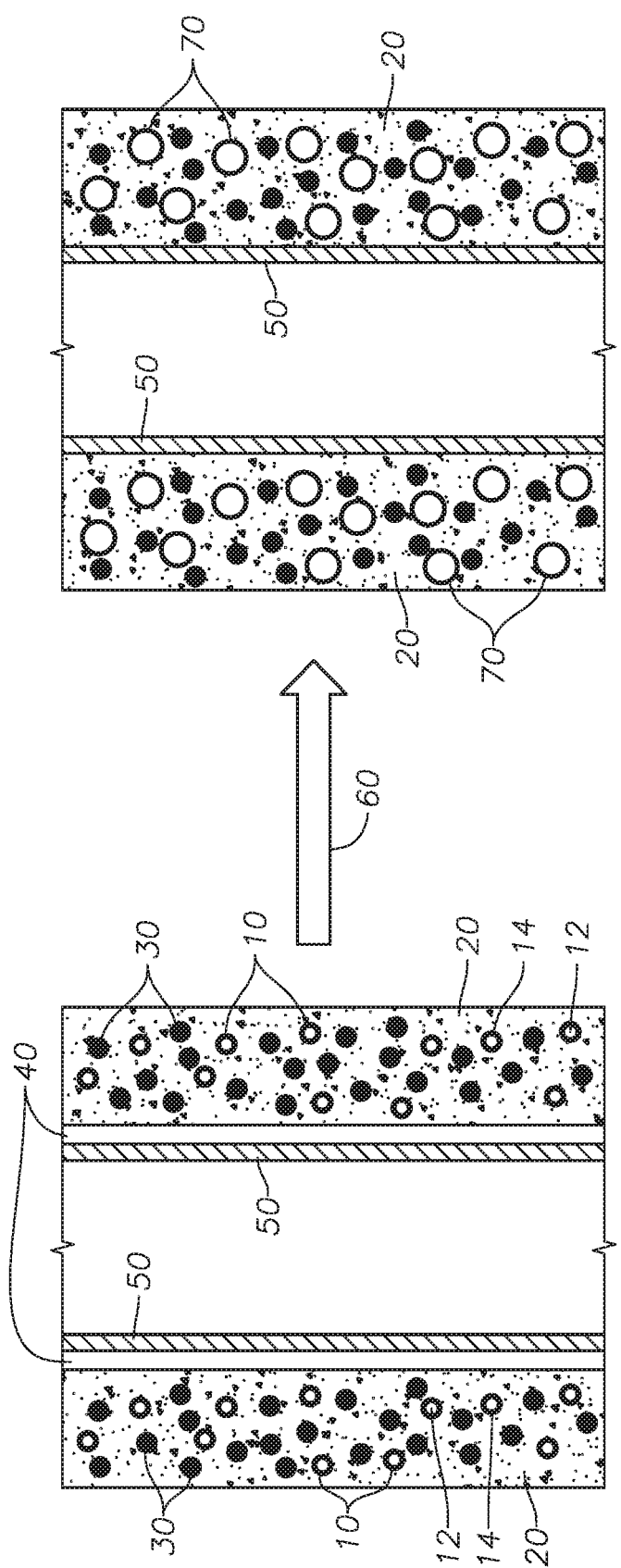
FIG. 2 provides a pictorial representation of an embodiment of the method of sealing propagating cracks.

The method for sealing propagating cracks is illustrated in FIG. 2. Encapsulated expanding agents 10 are dispersed throughout the sensor-laden cement sheath 20 along with water-filled vesicles 30. Encapsulated expanding agents 10 include on-demand expanding agents 12 and encapsulation compound 14. Propagating crack 40 occurs between casing wall 50 and sensor-laden cement sheath 20. When the measured value is greater than the activation threshold, heat source 60 is activated. As a result of heat source 60 being activated, the temperature in sensor-laden cement sheath 20 is increased to the activation temperature and the encapsulated expanding agents 10 react with water from the sensor-laden cement sheath 20 or water-filled vesicles 30 to produce swelled agents 70. Swelled agents 70 expand forcing sensor-laden cement sheath 20 toward casing wall 50 sealing the propagating crack.

Although the embodiments have been described in detail, it should be understood that various changes, substitutions, and alterations can be made hereupon without departing from the principle and scope. Accordingly, the scope of the embodiments should be determined by the following claims and their appropriate legal equivalents.

There various elements described can be used in combination with all other elements described here unless otherwise indicated.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed here as from about one particular value to about another particular value and are inclusive unless otherwise indicated. When such a range is expressed, it is to be understood that another embodiment is from the one particular value to the other particular value, along with all combinations within said range.

As used here and in the appended claims, the words "comprise," "has," and "include" and all grammatical variations thereof are each intended to have an open, non-limiting meaning that does not exclude additional elements or steps.

That which is claimed is:

1. A method of sealing propagating cracks in a sensor-laden cement sheath comprising the steps of:
    monitoring an electrical resistivity of the sensor-laden cement sheath to produce a measured value, wherein the sensor-laden cement sheath comprises a conductive sensor, an on-demand expanding agent, and a cement;
    activating a heat source when the measured value of the electrical resistivity is greater than an activation threshold, such that the measured value that is greater than the activation threshold is operable to indicate propagating cracks in the sensor-laden cement sheath;
    increasing a temperature of the sensor-laden cement sheath with the heat source to an activation temperature, wherein the activation temperature is operable to initiate a reaction between the on-demand expanding agent and water, wherein the activation temperature is greater than a formation temperature;
    reacting the on-demand expanding agent with water to produce a swelled agent, wherein the swelled agent occupies a greater volume than the on-demand expanding agent; and
    sealing the propagating cracks in the sensor-laden cement sheath with the swelled agent.

2. The method of claim 1, wherein the step of monitoring an electrical resistivity of the sensor-laden cement sheath comprises the steps of:
    determining a measured value of an electrical resistivity of the sensor-laden cement sheath; and
    comparing the measured value of the electrical resistivity to an activation threshold, wherein the activation threshold is the electrical resistivity that corresponds to a minimum acceptable amount of propagating cracks in the sensor-laden cement sheath.

3. The method of claim 1, wherein the conductive sensor is selected from the group consisting of carbon nanotubes, carbon fibers, graphene, metal fibers, and combinations of the same.

4. The method of claim 1, wherein the on-demand expanding agent is selected from the group consisting of magnesium oxide, calcium oxide, and combinations of the same.

5. The method of claim 1, wherein the heat source is selected from the group consisting of a hot fluid, electricity applications, resistive heating, microwave applications, and combinations of the same.

6. The method of claim 1, wherein the sensor-laden cement sheath further comprises water-filled vesicles.

7. The method of claim 1, wherein the on-demand expanding agent further comprises an encapsulation compound.

8. The method of claim 7, wherein the encapsulation compound is selected from the group consisting of polymeric compounds, ceramic compounds, and combinations of the same.

\* \* \* \* \*